United States Patent [19]

Collins

[11] Patent Number: 4,534,903
[45] Date of Patent: Aug. 13, 1985

[54] PROCESS FOR THE PREPARATION OF SUBSTITUTED AMINO DIENES

[75] Inventor: Guy R. Collins, Walnut Creek, Calif.

[73] Assignee: The Dow Chemical Company, Midland, Mich.

[21] Appl. No.: 469,547

[22] Filed: Feb. 25, 1983

[51] Int. Cl.³ .................. C07C 120/00; C07C 101/20
[52] U.S. Cl. ........................ 260/465.5 R; 260/464; 260/465.4; 560/125; 560/171
[58] Field of Search ........... 260/465.5 R, 464, 465.4; 560/171, 125

[56] References Cited

PUBLICATIONS

Schnekenburger, et al., C.A., 98; 107131u, (1983).

Anghelide, et al., C.A., 81; (1974), 77429b.
Ferris, et al., C.A., 72; 9237b, (1970).
Bullock, E. and Gregory, B., *Canadian Journal of Chemistry*, vol. 43, pp. 332–336 (1965).
Sato, K. and Ōhashi, M., *Bull. Chem. Soc. Jap.*, vol. 42, pp. 2319–2323 (1969).

*Primary Examiner*—Joseph Paul Brust
*Attorney, Agent, or Firm*—Paul D. Hayhurst

[57] ABSTRACT

Prepare 4-amino-1,3-dicyano-2-methyl-1,3-pentadiene and related substituted aminodienes by contacting β-aminocrotononitrile and related substituted aminoalkenes with a base acceptor in a solvent under mild conditions.

20 Claims, No Drawings

PROCESS FOR THE PREPARATION OF SUBSTITUTED AMINO DIENES

BACKGROUND OF THE INVENTION

The present invention relates to the preparation of substituted dienes. More specifically, the invention relates to a process for the preparation of amine-substituted dienes.

The dienes produced by the process of the present invention are useful, among other things, as precursors to compounds which may be used as curing agents for epoxy resins. The compound 4-amino-1,3-dicyano-2-methyl-1,3-pentadiene (ADCMPD) has previously been synthesized, in exceptionally low yields, by Sato et al., *Bulletin of the Chemical Society of Japan*, Vol. 42, 2319–2323 (1969). The addition of β-aminocrotononitrile to polyphosphoric acid at room temperature gave a 13 percent yield of ADCMPD. Id. at 2321. The dropwise addition of acetyl chloride to a solutiion of β-aminocrotononitrile in absolute ether produced ADCMPD in a 31 percent yield. Id. at 2322. In view of the deficiencies of conventional processes, it would be highly desirable to provide a process which could produce ADCMPD and related dienes in high yields.

SUMMARY OF THE INVENTION

The present invention is such a high yield process involving contacting a substituted aminoalkene with a base acceptor in the presence of a solvent under reaction conditions such that a substituted aminodiene is formed. The process of the present invention produces the substituted aminodienes in yields unexpectedly higher than the yields of known methods of making the substituted aminodienes. The substituted aminodienes are useful chemical intermediates in the production of epoxy curing agents.

DETAILED DESCRIPTION OF THE INVENTION

The substituted aminoalkenes of the present invention are alkenes having an amino moiety bonded to one of the double-bonded carbon atoms. The substituted aminoalkene bears a cyano moiety or a moiety of the formula —COOR$_1$ wherein R$_1$ is alkyl. Preferably R$_1$ is lower alkyl of 1 to 6 carbon atoms, most preferably, R$_1$ is methyl. Cyano-aminoalkenes are the preferred aminoalkenes. Typical substituted aminoalkenes include 3-amino-2-butenenitrile (β-aminocrotononitrile) and 3-amino-2-pentenenitrile. Preferred substituted aminoalkenes may be represented generally by the formula:

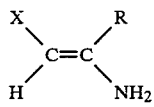   I wherein R is alkyl including cycloalkyl, and X is —CN or —COOR$_1$ wherein R$_1$ is as previously defined. More preferably, X is —CN and R is lower alkyl. Most preferably, R is methyl. Formula I is not meant to limit the preferred substituted aminoalkenes to the particular stereoisomers depicted, e.g., formula I is intended to represent both cis- and trans-isomers of the preferred substituted aminoalkenes.

A base acceptor is employed to advantage in the process of the present invention. The base acceptors of this invention are characterized by an acidic functionality and by their ability to shorten the time required to complete the reaction of this invention while maintaining or improving upon the yield of the corresponding reaction conducted in the absence of a base acceptor. The base acceptor typically is a strong non-mineral acid which is soluble in the reaction system. Examples of base acceptors include trifluoroacetic acid and trichloroacetic acid. Preferably, the base acceptor is a non-polymeric strong non-mineral acid. More preferred base acceptors have a pKa of less than about 0.3. Trifluoroacetic acid is the most preferred base acceptor. In the process of the present invention, the base acceptor is employed in an amount sufficient to stoichiometrically consume the ammonia which is given off as a by-product of the process of the present invention, thereby forming the corresponding salt. The salt is easily removed from the final reaction mixture; therefore, the final product is easily recovered. Typically, from about 0.5 to about 1.0 mole or more of base acceptor is employed per mole of substituted aminoalkene. Preferably, from about 0.55 to about 0.6 mole of base acceptor is employed per mole of substituted aminoalkene.

A solvent is advantageously employed in the process of the present invention. The solvent may be any inert material in which the substituted aminoalkene and base acceptor are soluble. Typical solvents include, for example, ethylene dichloride, carbon tetrachloride, toluene, methylene chloride, and acetone. Preferably, the solvent is a relatively aprotic material. Methylene chloride is the most preferred solvent. While the solvent may be employed in any amount which solubilizes the substituted aminoalkene and the base acceptor, the solvent is typically employed in amounts ranging from about 5 to about 50 moles of solvent per mole of substituted aminoalkene. Preferably, from about 5 to about 10 moles of solvent are employed per mole of substituted aminoalkene.

In general, any reaction temperature may be employed wherein the reaction kinetics are not deleterious to reaction rates, reaction time, or yield. Although the reaction temperature may be varied widely, the temperature for conducting the process of the present invention typically is in the range of from about 0° C. to about 100° C. Advantageously, the temperature is below the boiling point of the solvent, although the process may be conducted at reflux temperature. Preferably, the process will be conducted at from about 15° C. to about 45° C. The process pressure may be sub- or superatmospheric. Most preferably, the process is conducted at ambient temperature and pressure.

When the substituted aminoalkene, base acceptor, and solvent are combined under the conditions previously described herein, a substituted aminodiene is produced. Preferred substituted aminodienes may be represented generally by the formula:

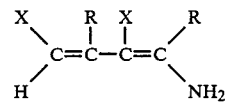   II wherein X and R are as previously defined herein. As with formula I, formula II is not intended to be limited to the specific stereoisomers depicted, except that the carbon atoms in the butadiene "backbone" will always be present as shown. The most preferred substituted aminodiene is ADCMPD. The process of the present invention is advantageous in that it may produce substituted aminodienes in higher yields than known methods. Preferably, the yield of substituted aminodiene will be at least about 40 percent. More preferably the yield will be at least about 75 percent, and most preferably at least about 90 percent.

SPECIFIC EMBODIMENTS

The following example is intended to illustrate the invention and should not be construed as limiting its scope.

EXAMPLE 1

A solution of 82 g of β-aminocrotononitrile and 500 ml of methylene chloride is prepared in a one-liter Ehrlenmeyer flask equipped with means for stirring and for temperature control. Then, trifluoroacetic acid (114 g) is added to the flask with cooling. A heavy, white precipitate forms immediately. The precipitate is collected on a filter and is washed with methylene chloride. The methylene chloride extracts are combined and evaporated to dryness to give a white, crystalline residue. The residue is recrystallized from ethanol and is vacuum dried to give 138 g of a white, crystalline product having a melting point of 166° C.–167° C. The product is 4-amino-1,3-dicyano-2-methyl-1,3-pentadiene, and the yield is 93.9 percent.

The preceding example illustrates that the process of the present invention proceeds in a straightforward manner to give a high yield of a very pure product which is easily isolated.

As previously mentioned, the preceding example serves only to illustrate the invention and its advantages, and it should not be interpreted as limiting since further modifications of the disclosed invention will be apparent to those skilled in the art. All such modifications are deemed to be within the scope of the invention as defined by the following claims.

What is claimed is:

1. A process comprising contacting an aminoalkene of the formula:

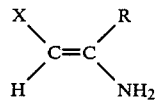

wherein R is alkyl or cycloalkyl, and wherein X is —CN or —COOR$_1$ wherein R$_1$ is alkyl; with a strong non-mineral acid in the presence of a solvent under reaction conditions such that there is formed an aminodiene of the formula:

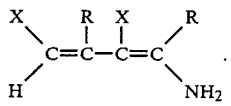

2. The process of claim 1 wherein the acid is a strong nonpolymeric organic acid.

3. The process of claim 1 wherein X is —CN and R is lower alkyl of from 1 to 6 carbon atoms.

4. The process of claim 3 wherein the acid has a pKa of less than about 0.3.

5. The process of claim 4 wherein R is methyl.

6. The process of claim 5 wherein the solvent is methylene chloride and the acid is trifluoroacetic acid.

7. The process of claim 6 wherein 4-amino-1,3-dicyano-2-methyl-1,3-pentadiene is produced in a yield of at least about 40 percent.

8. The process of claim 1 wherein 4-amino-1,3-dicyano-2-methyl-1,3-pentadiene is produced in a yield of at least about 40 percent.

9. The process of claim 1 wherein the substituted aminodiene is produced in a yield of at least about 40 percent.

10. The process of claim 1 wherein the substituted aminodiene is produced in a yield of at least about 75 percent.

11. The process of claim 1 wherein the substituted aminodiene is producing in a yield of at least about 90 percent.

12. A process comprising contacting β-aminocrotononitrile with trifluoroacetic acid in the presence of a solvent under reaction conditions such that there is formed 4-amino-1,3-dicyano-2-methyl-1,3-pentadiene.

13. The process of claim 12 wherein the solvent is methylene chloride.

14. The process of claim 12 wherein the yield of 4-amino-1,3-dicyano-2-methyl-1,3-pentadiene is at least about 40 percent.

15. The process of claim 12 wherein the yield of 4-amino-1,3-dicyano-2-methyl-1,3-pentadiene is at least about 75 percent.

16. The process of claim 12 wherein the yield of 4-amino-1,3-dicyano-2-methyl-1,3-pentadiene is at least about 90 percent.

17. A process comprising contacting an aminoalkene of the formula:

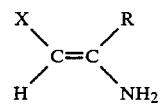

wherein R is alkyl or cycloalkyl, and wherein X is —CN or —COOR$_1$ wherein R$_1$ is alkyl; with a base acceptor in the presence of a solvent under reaction conditions such that there is produced in a yield of at least about 40 percent an aminodiene of the formula:

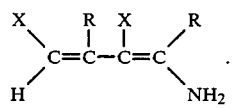

18. A process of claim 17 wherein the yield is at least about 75 percent.

19. The process of claim 18 wherein the yield is at least about 90 percent.

20. The process of claim 17 wherein the base acceptor has a pK$_a$ of less than about 0.3.

* * * * *